US009295825B2

(12) United States Patent
Biddell et al.

(10) Patent No.: US 9,295,825 B2
(45) Date of Patent: Mar. 29, 2016

(54) CONNECTOR, CONNECTOR SYSTEM AND USE THEREOF (75) Inventors: Christopher Biddell, Glos (GB); Winfried Kuhlmann, Melsungen (DE); Colin Kalman Lanyi, Glos (GB); Oscar-Werner Reif, Hannover (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 465 days.

(21) Appl. No.: 11/918,107

(22) PCT Filed: Apr. 28, 2006

(86) PCT No.: PCT/EP2006/003958
§ 371 (c)(1),
(2), (4) Date: Oct. 9, 2007

(87) PCT Pub. No.: WO2006/117138
PCT Pub. Date: Nov. 9, 2006

(65) Prior Publication Data
US 2009/0050213 A1 Feb. 26, 2009

(30) Foreign Application Priority Data
May 3, 2005 (DE) .......................... 10 2005 020 648

(51) Int. Cl.
*A61M 39/10* (2006.01)
*A61M 39/14* (2006.01)
(Continued)

(52) U.S. Cl.
CPC ........... *A61M 39/1011* (2013.01); *A61M 39/14* (2013.01); *A61M 39/18* (2013.01); *F16L 37/26* (2013.01); *A61M 2039/1027* (2013.01); *F16L 2201/44* (2013.01); *Y10T 137/0402* (2015.04)

(58) Field of Classification Search
CPC . A61M 39/1011; A61M 39/18; A61M 39/14; A61M 2039/1027; F16L 37/26; F16L 2201/44
USPC ................ 285/325, 103, 81, 89, 67, 326, 327
See application file for complete search history.

(56) References Cited

U.S. PATENT DOCUMENTS 154,536 A * 8/1874 Wolf .............................. 285/325
218,723 A * 8/1879 Faust ............................ 403/336
(Continued)

FOREIGN PATENT DOCUMENTS

DE    199 46 843 A1    5/2000
DE    102 55 817 A1    6/2004
(Continued)

*Primary Examiner* — Daniel P Stodola
*Assistant Examiner* — Zachary Dragicevich
(74) *Attorney, Agent, or Firm* — Gerald E. Hespos; Michael J. Porco; Matthew T. Hespos (57) ABSTRACT A connector assembly has a connector (10) with a fluid leadthrough (20) and a contact device (14). The contact device has an essentially planar contact surface (16) and a fluid leadthrough opening (18) passing through the contact surface (16). A sterile covering (64) sterilely covers at least part of the contact surface (16) and/or an end of the fluid leadthrough opening (20) adjacent the contact surface (16). A coupling device (22) is provided in proximity to the contact surface (16) outwardly from the fluid leadthrough opening (18). The connector assembly further includes a complementary connector (12) with a complementary coupling device (34) that can engage with the coupling device (22) along a coupling direction (40) that is essentially parallel to the contact surface (16).

6 Claims, 3 Drawing Sheets (51) Int. Cl.
  *A61M 39/18* (2006.01)
  *F16L 37/26* (2006.01)

(56) References Cited

U.S. PATENT DOCUMENTS

| | | | |
|---|---|---|---|
| 283,771 A * | 8/1883 | Genin | 285/325 |
| 309,444 A * | 12/1884 | Dunning | 285/327 |
| 531,071 A * | 12/1894 | Stahley | 285/325 |
| 657,037 A * | 8/1900 | Spickelmier | 285/325 |
| 823,346 A * | 6/1906 | Maxwell | 285/325 |
| 1,002,774 A * | 9/1911 | Stouffer | 285/86 |
| 1,285,543 A * | 11/1918 | Yarnell et al. | 285/67 |
| 1,300,569 A * | 4/1919 | Bundy | 174/152 S |
| 1,806,788 A * | 5/1931 | Cross et al. | 285/327 |
| 2,193,199 A * | 3/1940 | McKee | 285/70 |
| 3,812,659 A * | 5/1974 | Westergren et al. | 55/375 |
| 4,187,846 A | 2/1980 | Lolachi et al. | |
| 4,265,280 A | 5/1981 | Ammann et al. | |
| 4,418,945 A * | 12/1983 | Kellogg | 285/70 |
| 4,576,199 A | 3/1986 | Svensson et al. | |
| 4,600,221 A * | 7/1986 | Bimba | 285/91 |
| 5,383,691 A * | 1/1995 | Anthony | 285/325 |
| 5,586,792 A * | 12/1996 | Kalahasthy et al. | 285/319 |
| 5,788,291 A * | 8/1998 | Williams et al. | 285/325 |
| 5,958,338 A | 9/1999 | Lindsay et al. | |
| 6,077,259 A | 6/2000 | Caizza et al. | |
| 2003/0030272 A1 | 2/2003 | Johnson et al. | |
| 2006/0015063 A1 | 1/2006 | Butikofer et al. | |
| 2006/0033334 A1 | 2/2006 | Weber et al. | |
| 2006/0252298 A1 * | 11/2006 | Biddel et al. | 439/405 |

FOREIGN PATENT DOCUMENTS

| | | |
|---|---|---|
| DE | 20 2004 012 714 U1 | 12/2004 |
| FR | 1 223 094 | 6/1960 |
| WO | WO 86/05568 | 9/1986 |
| WO | WO 98/50105 | 11/1998 |

* cited by examiner

FIG 1

CONNECTOR, CONNECTOR SYSTEM AND USE THEREOF

The present invention relates to a connector, a connector system for the fluid-tight connection of a fluid supply of a connector to a fluid discharge of a complementary connector and the use of a connector and a complementary connector for the sterile connection of a fluid supply of the connector to a fluid discharge of the complementary connector.

A large number of connectors have been developed, for example for the purpose of handling biological fluids and/or liquids such as blood plasma. It is important in this respect for the characteristics of the fluid to remain unchanged in conjunction with leading the fluid through connectors. In particular, it is frequently necessary to protect the fluids from environmental influences, for example if the connectors are used in non-sterile surroundings. After connecting the connectors to one another, it is usually necessary to ensure that the fluid that is led through the connectors is not exposed to any environmental influences and, in particular, that it is not contaminated. In other words, it is frequently necessary, even though the connectors are being handled in non-sterile surroundings, to enable a sterile connection to be made between two connectors.

One object of the invention is to enable a sterile connection to be made by simple means. This object is achieved by a connector system capable of being connected in a fluid-tight manner to a container.

One feature of the present invention is to propose a connector with
- a fluid leadthrough;
- a contact device having an essentially planar contact surface and a fluid leadthrough opening, which is designed for leading fluid through, the fluid leadthrough opening passing through the contact surfaces;
- a sterile covering designed for sterilely covering, at least in part, the contact surface and/or an end of the fluid leadthrough opening facing towards the contact surface, and
- a coupling device, which is designed for engaging with a complementary coupling device of a complementary connector along a coupling device, the coupling direction being essentially parallel to the contact surface.

The expression "essentially planar" in the sense of the invention is understood to denote that the contact surface is preferably a planar surface. The contact surface can deviate from an ideal planar contact surface in the geometrical sense, however. In particular, the contact surface is a planar contact surface in the context of manufacturing accuracy. The term "essentially" in the sense of the invention is thus synonymous, for example, with the term in the context of manufacturing accuracy.

The term "sterile" is used in this invention with its conventional meaning, that is to say, for example, germ-free or unfruitful or infertile. Germ-free need not denote the total absence of germs and/or foreign bodies, however, but may include a predetermined or predeterminable maximum number of germs and/or foreign bodies. For example, the term "sterile" may denote a maximum number of germs at a level that is permitted or required according to accepted industrial standards.

Advantageously, a connection between a connector according to the invention and a complementary connector can be made using a single hand. This is the case in particular when, according to the invention, the coupling device of the connector is designed in such a way that, in the event of the coupling of the connector with the complementary connector, the contact surfaces of the contact devices in each case preferably lie essentially one on top of the other, and the contact surfaces are displaced in relation to one another. The distance of the contact surfaces from one another must not be changed in order to permit the connection of the connector to the complementary connector.

For example, the connector can exhibit an essentially cylindrical fluid leadthrough. The essentially planar contact surface of the contact device can be arranged in such a way in each case that the contact surface is essentially perpendicular to a cylinder axis of the fluid leadthrough. In particular, the fluid leadthrough discharges into the fluid leadthrough opening of the contact device. In conjunction with this, the contact device can be arranged at one end of the fluid leadthrough. However, the fluid leadthrough can also pass through the contact device via the fluid leadthrough opening.

The essentially planar contact surface of the connector preferably makes contact with the essentially planar contact surface of the complementary connector and preferably over the entire surface. In particular, the contact surface of the contact device is designed in such a way that it touches the contact surface of the contact device of the complementary connector and then, by being caused to move in the coupling direction, the coupling device of the connector enters into engagement with the complementary coupling device of the complementary connector. In other words, the contact surface of the connector and the contact surface of the complementary connector cannot be separated from one another in a direction perpendicular to the coupling direction, that is to say they already lie one on top of the other at least partially, and the connector or the complementary connector are then caused to move in the coupling direction, in conjunction with which the coupling device of the connector enters into engagement with the complementary coupling device of the complementary connector. This can be the case in particular if the coupling device and the contact device are executed in a single piece, that is to say the contact surface is a surface of the coupling device.

In order to protect the fluid which passes through the fluid leadthrough of the connector from external environmental influences, the contact surface and/or the end of the fluid leadthrough facing towards the contact surface is sterilely covered at least partially with a sterile covering. It is possible, for example, for only the end of the fluid leadthrough to be sterilely covered, but for the contact surface not to be sterilely covered. This can be the case if the fluid leadthrough exhibits a large wall thickness, for example. The contact surface is preferably covered with the sterile covering at least in a partially sterile manner, however, and this is the case in particular if the fluid leadthrough does not pass completely through the contact device. For example, the fluid leadthrough can be a plastic tube, which is permanently connected to a surface of the contact device situated opposite the contact surface in such a way that the tube discharges into the fluid leadthrough opening.

Furthermore, the fluid leadthrough opening of the connector and the fluid leadthrough opening of the complementary connector are positioned essentially opposite one another once the coupling device of the connector has essentially entered completely into engagement with the complementary coupling device of the complementary connector. The contact surfaces in this case are arranged in such a way, for example, that the fluid leadthrough is separated from the surrounding environment in a fluid-tight and sterile manner.

The connector preferably comprises a locking device, furthermore, which is designed to lock the connector to the complementary connector.

The locking device can be executed in such a way, for example, that it locks the connector to the complementary connector in the coupling direction and/or another direction, for example a direction perpendicular to the coupling direction and/or a direction parallel to a through-flow direction of the fluid.

A particular preference exists for the contact device and/or the coupling device and/or the locking device to be executed in a single piece.

There is a further preference for the coupling device to exhibit a coupling opening, and for the coupling device to be designed in such a way, furthermore, as to receive the complementary coupling device of the complementary connector through the coupling opening, and for the locking device to be designed in such a way as to close the coupling opening at least partially.

In other words, the complementary coupling device of the complementary connector is capable of being brought into engagement with the coupling device of the connector along the coupling direction, in conjunction with which the complementary coupling device is capable of being passed through a coupling opening in the coupling device of the connector. The coupling opening of the coupling device of the connector can be a round or rectangular opening, for example, in the coupling device. However, the coupling opening can also be a cut-out recess in the coupling device. The locking device is preferably arranged in such a way that the coupling opening is capable of being closed by means of the locking device.

The locking device is preferably arranged in such a way as to be capable of displacement essentially perpendicularly in relation to the coupling direction.

For example, the locking device can also be arranged in such a way as to be capable of displacement parallel to the fluid leadthrough.

In order to bring the coupling device into engagement with the complementary coupling device of the complementary connector, the locking device must be arranged preferably at a distance from the coupling opening in the direction perpendicular to the coupling direction. If the coupling device and the complementary coupling device are essentially fully in engagement, the locking device is capable of displacement perpendicularly in relation to the coupling direction, as a result of which the coupling opening is closed at least partially and the coupling device can no longer be released from the complementary coupling device.

In other words, the locking device is preferably designed in such a way that the complementary connector is essentially capable of being secured in the coupling direction.

The expression "capable of being secured in the coupling direction" in the sense of this invention is understood to denote, for example, that, in the presence of normal operating forces, a movement of the complementary connector relative to the connector in the coupling direction is suppressed completely.

A particular preference exists for the locking device to be a screw locking device.

The locking device is capable of displacement, for example, along a fluid leadthrough and is arranged in such a way as to be capable of rotating about the fluid leadthrough at the same time.

Furthermore, the coupling device is preferably designed in such a way that the connector and the complementary connector are essentially capable of being secured in a direction perpendicular to the coupling direction.

In other words, the coupling device and the complementary coupling device are in engagement in such a way that a movement of the coupling device relative to the complementary coupling device in a direction perpendicular to the coupling direction is essentially completely suppressed in the presence of normal operating forces. This is made possible, for example, by the fact that surfaces and/or shoulders of the coupling device and the complementary coupling device lie on top of one another and/or engage in one another, in conjunction with which the shoulders and/or the surfaces are arranged essentially parallel to the contact surface of the connector and/or the complementary connector. For example, the coupling device and the complementary coupling device can exhibit a system of rails, which is arranged in the coupling direction, that is to say parallel to the contact surface. The rails can engage in one another, for example, as a consequence of which a movement perpendicular to the coupling direction is essentially not possible, although on the other hand a movement parallel to the coupling direction is capable of being executed.

In addition, the coupling device is preferably designed in such a way that the connector and the complementary connector are capable of being secured in a releasable manner along the coupling direction.

In other words, in a coupled state, that is to say when the coupling device and the complementary coupling device have essentially moved completely into engagement, the coupling device and the complementary coupling device are essentially unmovable when subjected to the application of force up to a predeterminable maximum force in the coupling direction. If the predetermined maximum force, which corresponds to an operating force, is nevertheless exceeded, the coupling device can be released from the complementary coupling device against the direction of coupling, that is to say the connector and the complementary connector can be released from one another. This is only possible, of course, if the connector and the complementary connector are not locked by means of the locking device.

The connector is preferably capable of being connected to a container in a fluid-tight manner. The connector in this case can be connected directly to the container. In other words, the fluid leadthrough of the connector is connected directly to the container preferably in a sterile manner. The connector in this case can be connected to the complementary connector by means of the coupling device, that is to say an opening in the fluid leadthrough is connected preferably in a sterile manner to the fluid leadthrough of the complementary connector. A further opening in the fluid leadthrough is connected to the container preferably in a sterile manner. The connection between the container and the connector can also be effected via a hose. The connector can be arranged on the container in a releasable manner, for example, and/or can be connected to it.

Consequently, a fluid can pass from the container, if necessary by means of a hose, through the connector and the complimentary connector and can be transferred, for example, into a container connected to the complementary connector. However, the complementary connector can also be connected to the blood circulatory system of a living being, for example a mammal and in particular a human being, preferably by means of a hose or a hose system. In particular, the direction of flow through the connector and/or the complementary connector can also take place in the opposite direction, that is to say in this sequence, for example, starting from a container, through the complementary connector, through the connector and then into the container connected with the connector. In other words, the container connected to the connector can be filled and/or emptied by means of the fluid flow through the connector.

The container is preferably a bioreactor, a bag or a filter body, and especially preferred a filter capsule. A further preference exists for the connection between the connector and the container to be sterile.

According to a further feature of the present invention, a connector system is proposed for the fluid-tight connection of a fluid supply of a connector to a fluid discharge of a complementary connector, in conjunction with which the connector and the complementary connector in each case is embodied according to the invention.

A further feature of the present invention concerns the use of a connector and a complementary connector for the sterile connection of a fluid supply of the connector to a fluid discharge of the complementary connector involving the following steps:

provision of a connector according to the invention and a complementary connector according to the invention;
coupling of the coupling device and the complementary coupling device in the coupling direction, in such a way that the contact surfaces of the contact devices are in fluid-tight contact with one another, and
removal of the sterile coverings.

For example, the connector and the complementary connector can be brought together in a direction perpendicular to the coupling direction until the contact surfaces, that is to say the contact surface of the contact device of the connector and the complementary contact surface of the complementary contact device of the complementary connector, make contact with one another at least partially. The coupling devices are brought into engagement by causing the connector and the complementary connector to be displaced along the coupling direction, in conjunction with which the contact surfaces preferably remain in contact. Furthermore, the coupling device and the complementary coupling device are preferably embodied in such a way that the contact surfaces press against or are pressed against one another with a predeterminable force when the coupling device and the complementary coupling device are brought into engagement and/or have essentially entered completely into engagement. A particular preference exists for the contact surfaces to be in contact with one another essentially completely. A fluid-tight contact is established in particular between the contact surfaces and consequently between the connector and the complementary connector.

In connection with this, the sterile coverings, which are still present between the two contact surfaces, can be pulled out, in conjunction with which the sterile coverings are preferably removed in a direction running essentially parallel to the coupling direction. If, for example, the complementary coupling device is passed through a coupling opening in the coupling device with the coupling device of the connector in conjunction with the coupling procedure, the sterile coverings are preferably removed through the coupling opening.

Following removal of the sterile coverings, the connector is locked to the complementary connector by means of the locking device and the complementary locking device. Locking the connector to the complementary connector prevents the coupling device and the complementary coupling device from becoming uncoupled. In addition, the connection of the connector to the complementary connector is stabilized, as a consequence of which the connection can be subjected to quite large forces, in conjunction with which the connection continues to be fluid-tight, and the fluid remains protected from environmental influences.

The invention is described below by way of example with reference to the accompanying drawings of preferred embodiments, in which.

Figure 1:
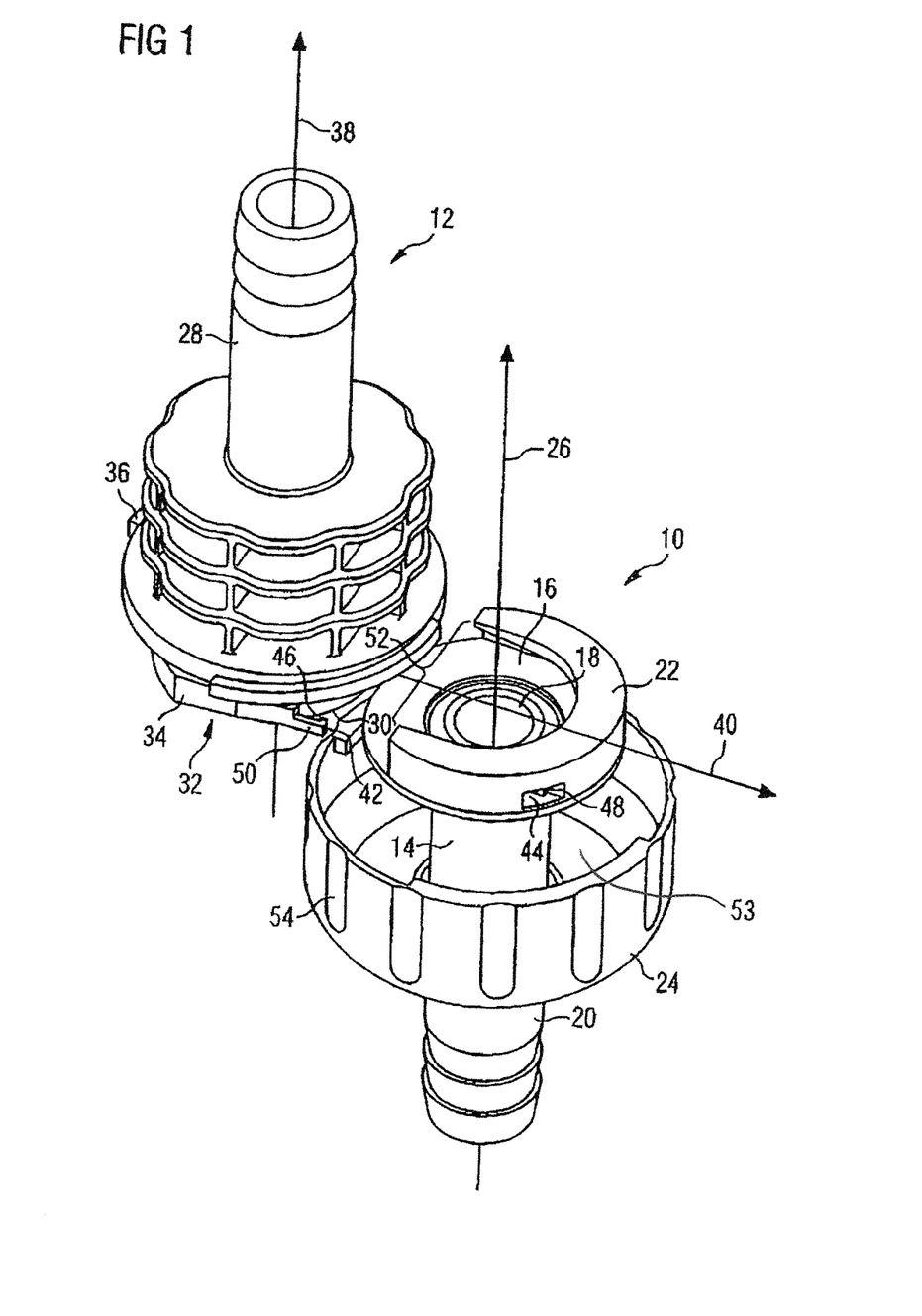
FIG. 1: depicts a perspective schematic view of a preferred connector system.

FIG. 1 depicts a connector system with a preferred connector 10 and a preferred embodiment of a connector 12 complementary thereto. The connector 10 comprises a contact device 14 having a contact surface 16 and a rear surface 17 opposite the contact surface 16. The contact device 14 additionally comprises a fluid leadthrough opening 18, in conjunction with which a tube 20 as a preferred fluid leadthrough discharges into the fluid leadthrough opening 18. Also depicted in FIG. 1 is coupling device 22. In the preferred embodiment of the connector 10 depicted in FIG. 1, the contact device 14, the tube 20 and the coupling device 22 are manufactured in a single piece. Furthermore, the connector 10 comprises a nut 24 as a preferred locking device. The nut 24 includes a planar flange 53 with a central opening that surrounds the tube 20 and a substantially cylindrical side wall 54 that extends perpendicularly from the planar flange 53 and substantially concentrically with the tube 20. The nut 24 is so arranged as to be capable of displacement relative to the tube 20. In particular, the nut 24 can be displaced along an axial direction 26 of the tube 20. Furthermore, the nut 24 can be turned or caused to rotate about the axial direction 26 of the tube 20. In addition, the contact surface 16 of the contact device 14 is arranged essentially perpendicularly to the axial direction 26.

Furthermore, the complementary connector 12 is represented schematically in FIG. 1. The complementary connector 12 comprises a tube 28 as a preferred fluid leadthrough and a complementary contact device 30. The complementary contact device 30 also exhibits a complementary contact surface 32. In addition, a complementary coupling device 34 of the complementary connector 12 is depicted in FIG. 1. The tube 28, the complementary contact device 30, the complementary contact surface 32 and the complementary coupling device 34 are preferably manufactured in a single piece. Furthermore, a thread 36 is represented as a preferred complementary locking device in FIG. 1. There is a particular preference for the tube 28, the complementary contact device 30, the complementary contact surface 32, the complementary coupling device 34 and the thread 36 to be manufactured in a single piece. It is not necessary, however, for the tube 28, the complementary contact device 30, the complementary contact surface 32, the complementary coupling device 34 and the thread 36 of the complementary connector 12 to be manufactured in a single piece. On the contrary, the individual component parts can also be manufactured separately from one another and, for example, glued together, screwed, or connected to one another in some other way. The same is also true for the connector 10. Furthermore, an axial direction 38 of the tube 28 of the complementary connector 12 is represented in FIG. 1. The complementary contact surface 32 is preferably arranged at an essentially perpendicular angle to the axial direction 38 of the tube 28. Alternatively, the complementary contact surface 32 can also be arranged at an angle other than 90° to the axial direction 38 of the tube 20. Analogously, the contact surface 16 of the connector 10 can also be arranged at an angle other than 90° to the axial direction 26 of the tube 20. For example, both the complementary contact surface 32 and the axial direction 38 can be arranged at an angle of around 45°. The contact surface 16 and the axial direction 26 of the connector 10 can also be arranged at an angle of around 45°. If the connector 10 and the complementary connector 12 are connected to one another, the tubes 20, 28 can be arranged at an angle essentially of around 90°, for example. The tubes 20, 28 can also be arranged parallel to one another, although offset in relation to one another.

A coupling direction 40 is depicted in addition in FIG. 1. The coupling direction 40 is preferably essentially perpendicular to the axial direction 26 and the axial direction 38. The complementary connector 12 can be caused to move, for example, along the coupling direction 40 towards the connector 10, in conjunction with which the complementary contact surface 32 and the contact surface 16 preferably make contact with one another. If the coupling device 22 and the complementary coupling device 34 are brought into engagement, the contact surface 16 and the complementary contact surface 32 will lie essentially one on top of the other. The contact surface 16 and the complementary contact surface 32 preferably lie on top of one another essentially with positive engagement, in conjunction with which the tubes 20, 28 similarly lie adjacent to one another with positive engagement. If the contact device 14 and the complementary contact device 30 are essentially completely in engagement, hooks 42 on the complementary contact device 30 pass through openings 44 in the contact device 14, in conjunction with which a projection 46 on each hook 42 engages in each case behind a shoulder 48 on each opening 44. Each hook 42 is preferably arranged on an arm 50 that is capable of resuming its original shape. If the complementary coupling device 34 is brought into engagement with the coupling device 22, each of the arms 50 that is capable of resuming its original shape will be deflected preferably perpendicularly to the coupling direction 40 until the projection 46 is present in the coupling direction 40 behind the shoulder 48. Because of the ability of the arm 50 to resume its original shape, the arm 50 that is capable of resuming its original shape moves back essentially to its original position, as a consequence of which the projection 46 engages behind the shoulder 48. The complementary coupling device 34 is accordingly secured to the coupling device 22, that is to say a movement of the complementary coupling device 34 against the coupling direction 40 is not possible in normal operation. Only if a force greater than the normal operating state is applied to the complementary connector 12 against the coupling direction 40, can the complementary connector 12 be uncoupled from the connector 10. The connector 10 and the complementary connector 12 can be coupled to one another in such a way, for example, that even a very small force is sufficient to separate the connector 10 and the complementary connector 12 from one another. The connector 10 and the complementary connector 12 are simply coupled to one another, for example, in order for the locking by means of the nut 24 and the thread 36 to be simplified.

Alternatively, it is also possible, for example, for only one hook 42 and one opening 44 to be provided, in conjunction with which the hook 42 and opening 44 are arranged in such a way that they are positioned essentially along the coupling direction 40 on the complementary connector 12 and/or the connector 10. Furthermore, it is also possible for the connector 10 and the complementary connector 12 to be secured to one another by means of some other device. It is possible, in particular, for the connector 10 and the complementary connector 12 to exhibit an identical structural shape.

In particular, the complementary coupling device 34 is brought into engagement with the coupling device 22 through a coupling opening 52 for the coupling device 22 along the coupling direction 40. As soon as the coupling device 22 and the complementary coupling device 34 have been secured to one another, the nut 24 can be displaced along the axial direction 26 of the tube 20, and the nut 24 can be screwed onto the thread 36. Because of the screwed connection, movement of the complementary coupling device 34 against the coupling direction 40 relative to the coupling device 22 is no longer possible. As a consequence of this, movement of the connector 10 relative to the complementary connector 12 along the axial directions 26, 38 is no longer possible, both because of the coupling device 22 and the complementary coupling device 34, and because of the screwed connection of the nut 24 on the thread 36. Movement of the connector 10 relative to the complementary connector 12 along the coupling direction 40, that is to say in and against the coupling direction 40, is also not possible, since the coupling opening 52 is closed off at least partially by a side wall 54 of the nut 24.

In place of the nut 24 and the thread 36, the connector 10 and the complementary connector 12 can also be locked to one another by a snap-in fastener and/or a hook-and-eye fastener or any other conventional fastener, for example of a kind used to secure the coupling device 22 to the complementary coupling device 34, as a result of which a relative movement of the connector 10 and the complementary connector 12 along the coupling direction 40 and/or the axial directions 26, 38 is prevented.

The connector 10 depicted in FIG. 1 is situated downstream of the complementary connector 12, for example, in terms of a through-flow direction of the fluid. The fluid leadthrough opening 56 of the complementary connector 12 thus corresponds to a fluid discharge of the complementary connector 12. The fluid leadthrough opening 18 of the connector 10 corresponds to a fluid supply of the connector 10. Alternatively, the through-flow direction of the fluid can also be changed, and/or the connector 10 can be replaced by the complementary connector 12.

Figure 2:
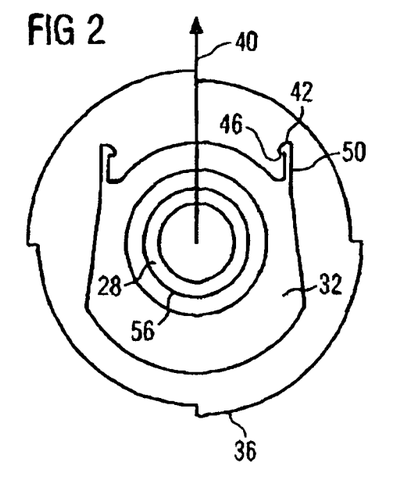
FIG. 2: depicts a view from above of a preferred connector.

FIG. 2 depicts a view from above of the complementary connector 12. As can be appreciated from FIG. 2, the complementary contact surface 32 has a fluid leadthrough opening 56, in conjunction with which the tube 28 of the complementary connector 12 discharges into the fluid leadthrough opening 56. Also depicted in FIG. 2 are the two arms 50 that are capable of resuming their original shape, each of which terminates in the hooks 42, as well as the thread 36, which can be screwed together with the nut 24 of the connector 10 for the purpose of locking the complementary connector 12 to the connector 10.

Figure 3:
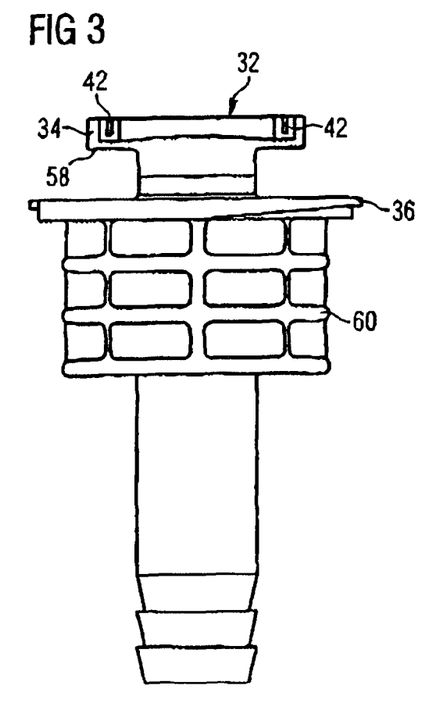
FIG. 3: depicts a schematic view of the connector according to FIG. 2.

FIG. 3 illustrates a schematic side view of the complementary connector 12. In particular, FIG. 3 illustrates the side of the complementary connector 12, on which the hooks 42 of the arms 50 that are capable of resuming their original shape are arranged. Also illustrated in FIG. 3 is a shoulder 58 of the complementary coupling device 34. The shoulder 58 preferably lies opposite the complementary contact surface 32. For example, the shoulder 58 can be arranged parallel to the complementary contact surface 32. Furthermore, the thread 36 is illustrated in FIG. 3. As can be appreciated from FIG. 3, the thread 36 is designed in such a way that the connector 10 and the complementary connector 12 can be locked to one another, for example with a quarter of a turn of the nut 24. The thread 36 can also exhibit a large number of windings, for example, as a result of which the nut 24 can be screwed onto the thread 36 with one or more revolutions. Furthermore, FIG. 3 depicts a stiffening ring 60, which is preferably manufactured in a single piece with the thread 36 and is arranged on the complementary connector 12. The stiffening ring 60 serves the purpose, for example, of strengthening and stabilizing the thread 36. In addition, the complementary connector 12 can also be gripped and retained by the stiffening ring 60, for example.

Figure 4:
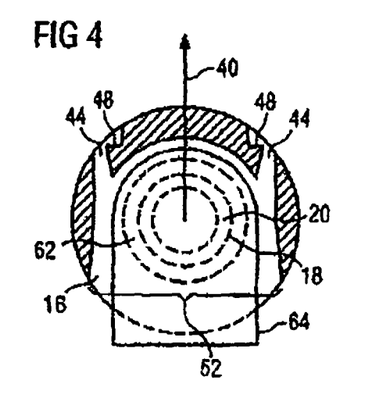
FIG. 4: depicts a sectioned view of a further preferred connector.

FIG. 4 depicts a sectioned view of the connector 10 along a plane that lies parallel to the contact surface 18 of the connector 10. The contact surface 16 is represented in FIG. 4. In addition, FIG. 4 shows the fluid leadthrough opening 18 and the tube 20, which discharges into the fluid leadthrough 18. Furthermore, a cut-out recess 62 in the contact surface 16 is illustrated in FIG. 4. The cut-out recess 62 serves the purpose, for example, of receiving a sealing means (not illustrated here), for example an o-ring or a silicon seal. A sealing means of this kind can be embodied in such a way, for example, that it projects above the contact surface 16. Analogously, the complementary contact surface 32 of the complementary connector 12 can exhibit a corresponding cut-out recess for a corresponding sealing means (see FIG. 2), for example. When the connector 10 and the complementary connector 12 are coupled to one another, corresponding sealing means will preferably enter into fluid-tight contact, as a result of which no fluid is able to escape laterally from the fluid leadthrough openings 18, 56 onto the contact surface 16 and/or the complementary contact surface 32. This also prevents fluid, which passes through the connector 10 and the complementary connector 12, from being contaminated by external environmental influences, for example, and prevents contamination from penetrating into the tubes 20, 28.

Furthermore, the coupling opening 52 is illustrated in FIG. 4. If the connector 10 is connected and/or secured to the complementary connector 12, that is to say if the coupling device 22 is brought into engagement with the complementary coupling device 34, the complementary coupling device 34 will pass through the coupling opening 52. Furthermore, in the event of the coupling together of the complementary coupling device 34 and the coupling device 22, the hooks 42 of the complementary coupling device 34 will pass through the openings 44, in conjunction with which, in the state in which they are completely coupled to one another, the projections 46 of the arms 50 of the complementary coupling device 34 that are capable of resuming their original shape engage behind the shoulders 48. Consequently, the complementary coupling device 34 and accordingly the complementary connector 12 can also be readily uncoupled from the coupling device 22 and/or the connector 10, if the coupling device 22 and the complementary coupling device 34 are not fully in engagement, that is to say if the projections 46 of the arms 50 that are capable of resuming their original shape do not engage behind the shoulders 48. If, on the other hand, the coupling device 22 and the complementary coupling device 34 have entered fully into engagement, the complementary coupling device 34 is secured to the coupling device 22. Consequently, the complementary connector 12 is also secured to the connector 10. In other words, the connector 10 and the complementary connector 12 cannot be caused to move relative to one another against the coupling direction by normal operating forces. If, however, a force exceeding normal operating forces is applied to the complementary connector 12 against the coupling direction 40 with the connector 10 securely retained, the connector 10 and the complementary connector 12 can be uncoupled from one another, in conjunction with which the complementary coupling device 34 again passes through the coupling opening 52 of the coupling device 22. The same is true if such a force is applied to the connector 10 with the complementary connector 12 securely retained.

Furthermore, a sterile covering 64 is preferably arranged in each case on the contact surface 16 and on the complementary contact surface 32. The sterile covering 64 can be a film, for example. In particular the contact surface 16 and the fluid leadthrough opening 18 are sterile. The tube 20 is also sterile.

Figure 5:
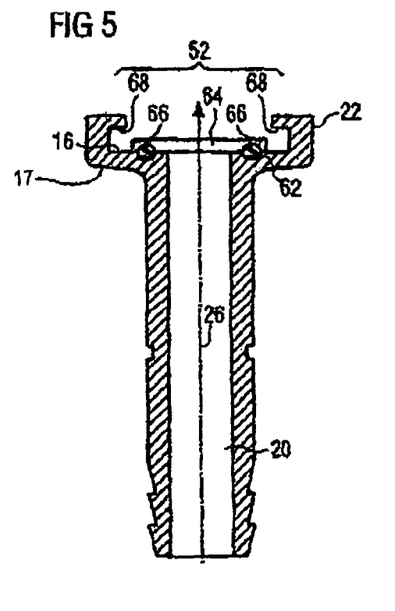
FIG. 5: depicts a further sectioned view of the connector according to FIG. 4.

FIG. 5 depicts a sectioned view of the connector 10 along a plane perpendicular to the coupling direction 40, which contains the axial direction 26 of the tube 20. Depicted in FIG. 5 is the cut-out recess 62, in which a sealing means 66 for fluid-tight sealing is arranged with a corresponding sealing means of the complementary connector 12. Furthermore, the coupling opening 52 is depicted in FIG. 5. As can be appreciated from FIG. 5, the coupling opening 52 does not exhibit a closed circumference. On the contrary, the coupling opening 52 is delimited only by two shoulders 68 on a side lying opposite the contact surface 16. If the complementary coupling device 34 is brought into engagement with the coupling device 22 through the coupling opening 52 in the coupling direction 40, the shoulders 58 of the complementary coupling device 34 and the shoulders 68 of the coupling device 22 will come into contact with one another. In particular, the shoulders 68 are separated from the contact surface 16 by a distance such that the complementary coupling device 34 is preferably an accurate fit in the coupling opening 52. As soon as the coupling device 22 and the complementary coupling device 34 enter into engagement, any movement of the connector 10 relative to the complementary connector 12 is restricted or prevented by the interlocking of the shoulders 68, 58. The shoulders 58 can be pressed against the shoulders 68 in particular thanks to the elastic sealing means 66, which is arranged in the cut-out recess 62 and in a corresponding cut-out recess in the complementary connector 12. This is the case in particular when the elastic sealing means 66 projects above the contact surface 16 in the axial direction 26 of the tube 20. It is also possible, for example, because of the distance of the shoulders 68 from the contact surface 16 and the dimensions of the complementary coupling device 34, for the sealing means 66 to be compressed against the axial direction 26, as a result of which the contact surface 16 and the complementary contact surface 32 make contact with one another over the entire surface. The tube 20 and the tube 28 are preferably sealed in a fluid-tight manner in relation to the outside thanks to the sealing means 66. In the event of an essentially all-over contact between the contact surface 16 and the complementary contact surface 32, it is not necessary, for example, to use a sealing means.

Furthermore, a sterile foil or a similar preferably elastic material can be stuck, for example, to at least one part of the area of the contact surface 16 as a preferred sterile covering 64. The sterile covering 64 is arranged in particular at least over the fluid leadthrough opening 18 and the sealing means 66. Analogously, a corresponding sterile covering 64 is also arranged on the complementary contact surface 32 of the complementary connector 12. In the operating state, the connector is connected to an end of the tube 20 opposite the coupling devices 22, for example with a hose (not illustrated here). The inside of the connector is protected in a sterile manner against environmental influences. The same is true, for example, of the complementary connector 12. If the connector 10 and the complementary connector 12 are coupled to one another, the sterile covering 64 of the connector 10 and the sterile covering (not illustrated here) of the complementary connector 12 are present between the contact surface 16 and the complementary contact surface 32 (and/or between corresponding sealing means 66). If the connector 10 and the complementary connector 12 are in a state in which they are completely coupled to one another, that is to say if the coupling device 22 has entered fully into engagement with the complementary coupling device 34, the sterile coverings 64 will project, for example against the coupling direction 40, through the coupling opening 52, both from the connector 10 and from the complementary connector 12. The sterile coverings 64 can be pulled out against the coupling direction 40 between the connector 10 and the complementary connector 12. As soon as the sterile coverings 64 have been removed, the contact surface 16 and the complementary contact surface 32 (and/or the corresponding sealing means) come into contact, in conjunction with which the contact is sterile. Consequently, the tube 20 of the connector 10 is connected sterilely to the tube 28 of the complementary connector 12, in conjunction with which in particular a fluid-tight closure of the two pipes 20, 28 against the surrounding environment and/or against environmental influences is produced, and this fluid-tight closure is sterile. Before, during and after the coupling of the connector 10 to the complementary connector 12, the fluid leadthrough openings 18, 56 and the internal surfaces of the tubes 20, 28 are accordingly sterile and are protected against contamination by external environmental influences, in conjunction with there is no requirement for an outside area of the sterile covering 64 and non-covered areas of the contact surfaces 16, 32 to be sterile.

In a coupled state, uncoupling against the coupling direction 40 is preferably prevented due to the engagement of the hooks 42 with the shoulders 48 at normal operating forces. Movement of the connector 10 relative to the complementary connector 12 is similarly not possible along or against the axial directions 26, 38 because of the shoulders 58, 68. In a completely coupled state, the connector 10 and the complementary connector 12 are consequently connected in such a way that a fluid exchange is possible through the fluid leadthrough openings 18, 56 between the tubes 20, 28. Contamination by external environmental influences and/or a fluid exchange with the surrounding environment is not possible, however. The connection between the connector 10 and the complementary connector 12 is further stabilized because of the nut 24 and the thread 36, in conjunction with which uncoupling against the coupling direction 40 in particular is essentially not possible because of the side wall 54 of the nut 24, including at forces which exceed normal operating forces.

The present connector 10 and/or the present complementary connector 12 are not restricted to the configurations described above. On the contrary, it is possible for the connector 10 and the complementary connector 12 to be of preferably identical execution. For example, the coupling device 22 of the connector 10 can exhibit only a single opening 44. An arm 50 that is capable of resuming its original shape with a hook 42 arranged thereon, as exhibited by the complementary connector 12, can be provided, for example, in place of the second opening 44. In a corresponding manner, the complementary connector 12 can exhibit an opening 44 with a projection 46 in place of an arm 50 that is capable of resuming its original shape and a hook 42 arranged thereon. Furthermore, the sterile covering 64 can cover the whole of the contact surface 16. However, the sterile covering 64 can also cover only a part of the area of the contact surface 16.

In addition, the nut 24 and the thread 36 can be replaced by some other locking device. For example, a snap-in fastener or a clamping fastener, which is preferably capable of being operated in a simple manner with a single hand, can be provided in place of the screwed fastener. It may be adequate, for example, for the locking device only to be capable of displacement, in conjunction with which the locking device is arranged on the connector 10, for example, and is not locked with a complementary corresponding part of the complementary connector 12, but rather only closes the coupling opening 56 at least partially.

Furthermore, the thread 36 can be so arranged as to be capable of displacement along the axial direction 38 of the tube 28, and/or the screw 24 can be so arranged as to be capable of displacement along the axial direction 26 of the tube 20.

LIST OF REFERENCE DESIGNATIONS 10 connector
12 complementary connector
14 contact device
16 contact surface
18 fluid leadthrough opening
20 tube
22 coupling device
24 nut
26 axial direction
28 tube
30 complementary contact device
32 complementary contact surface
34 complementary coupling device
36 thread
38 axial direction
40 coupling direction
42 hook
44 openings
46 projection
48 shoulder
50 arm that is capable of resuming its original shape
52 coupling opening
54 side wall
56 fluid leadthrough opening
58 shoulder
60 stiffening ring
62 cut-out recess
64 sterile covering
66 sealing means
68 shoulder

The invention claimed is:

1. A connector system comprising:
a connector (10) having an essentially planar contact surface (16) and a fluid leadthrough opening passing through the contact surface (16), a peripheral wall extending partly around the planar contact surface (16) and disposed outwardly from the fluid leadthrough opening (18), the peripheral wall having opposite ends spaced from one another and defining a coupling opening (52) therebetween, the peripheral wall having an outside diameter, a shoulder (68) extending radially in from the peripheral wall and facing the planar contact surface (16), two openings (44) passing through the peripheral wall at positions opposite the coupling opening (52) and between the shoulder (68) and the planar contact surface (16), the connector (10) further having a rear surface (17) facing substantially oppositely from the contact surface (16);
a sterile covering (64) sterilely and removably covering at least a part of the contact surface (16) and the fluid leadthrough opening (20), part of the sterile covering (64) projecting out beyond the contact surface (16) at a position opposite the opening (44);
a complementary connector (12) having an end and a complementary shoulder (58) adjacent the end, the complementary shoulder (58) being slidably insertable along a coupling direction (40) parallel to the contact surface (16) into a space inward of the peripheral wall of the connector (10) and between the contact surface (16)

and the shoulder (68), two arms (50) projecting from the complementary shoulder (58) parallel to the planar contact surface (16) and having hooks (42) projecting from leading end portions of the arms (50), the arms (50) being deflectable substantially parallel to the contact surface (16) and substantially perpendicular to the coupling direction (40), the hooks (42) engaging a part of the peripheral wall of the connector (10) adjacent the openings (44) of the peripheral wall for preventing movement of the complementary connector (12) in a direction against the coupling direction (40), an external thread (36) formed on a part of the complementary connector (12) spaced from the end of the complementary connector (12) and from the complementary shoulder (58) and disposed so that the shoulder (68) is between the complementary shoulder (58) and the part of the complementary connector (12) having the external thread (36) when the connector (10) and the complementary connector (12) are connected, the part of the complementary connector (12) with the external thread (36) having an outside diameter greater than the outside diameter of the peripheral wall of the connector (10); and a lock nut (24) having a flange (53) engaging the rear surface (17) of the connector (10) and an internally threaded sidewall (54) projecting from the flange (53), the internally threaded sidewall (54) threadedly engaging the external thread (36) of the complementary connector (12) while surrounding the peripheral wall and the shoulder (68) of the connector (10) and the complementary shoulder (58) of the complementary connector (12) for preventing movement between the complementary shoulder (58) and the contact surface (16).

2. The connector system as claimed in claim 1, in conjunction with which the connector (10) has a tube (20) defining the fluid leadthrough (16), the tube (20) extending from the rear surface (17) of the connector (10).

3. The connector system as claimed in claim 2 wherein the flange (53) of the lock nut (24) has a central opening that surrounds the tube (20) extending from the rear surface (17), the fluid leadthrough opening (18) extending through the tube (20).

4. The connector system as claimed in claim 1, wherein the hooks (42) project from surfaces of the arms (50) facing one another, each hook (42) having a projection surface (46) aligned substantially normal to the coupling direction (40), the peripheral wall of the connector (10) having locking shoulders (48) adjacent the openings (44) and aligned substantially normal to the coupling direction (40), the projection surfaces (46) of the hooks (42) being lockable to the locking shoulders (48) of the peripheral wall.

5. The connector system as claimed in claim 4, wherein the peripheral wall of the connector (10) has an outer circumferential surface, the locking shoulders (48) being inward of the outer circumferential surface.

6. The connector system as claimed in claim 1, wherein the sterile covering (64) is disposed sufficiently inward of the peripheral wall to avoid interference with the arms (50) when the complementary shoulder (58) is slidably inserted along the coupling direction (40) into a space inward of the peripheral wall of the connector (10) and between the contact surface (16) and the shoulder (68).

* * * * *